(12) United States Patent
Lonzetta et al.

(10) Patent No.: US 6,620,968 B1
(45) Date of Patent: Sep. 16, 2003

(54) HIGH HYDROCARBON SPACE VELOCITY PROCESS FOR PREPARING UNSATURATED ALDEHYDES AND ACIDS

(75) Inventors: Charles Michael Lonzetta, Houston, TX (US); James Edward Elder, Houston, TX (US); Peter David Klugherz, Huntingdon Valley, PA (US); Timothy Allen Hale, Houston, TX (US)

(73) Assignee: Rohm and Haas Company, Philadelphia, PA (US)

( * ) Notice: Subject to any disclaimer, the term of this patent is extended or adjusted under 35 U.S.C. 154(b) by 266 days.

(21) Appl. No.: 09/708,138

(22) Filed: Nov. 8, 2000

Related U.S. Application Data

(60) Provisional application No. 60/167,079, filed on Nov. 23, 1999.

(51) Int. Cl.[7] .................. C07C 51/235; C07C 27/10
(52) U.S. Cl. .................... 562/532; 562/512.2
(58) Field of Search ................. 562/512.2, 532

(56) References Cited

U.S. PATENT DOCUMENTS

| 3,775,474 A | 11/1973 | Ohara et al. |
| 3,798,264 A | 3/1974 | Kubota et al. |
| 3,893,951 A | 7/1975 | Grasselli et al. |
| 3,954,855 A | 5/1976 | Wada et al. |
| 3,988,213 A | 10/1976 | Yoshida et al. |
| 4,021,310 A | 5/1977 | Shimizu et al. |
| 4,025,565 A | 5/1977 | Oda et al. |
| 4,034,008 A | 7/1977 | Kurtz et al. |
| 4,075,127 A | 2/1978 | Kadowaki et al. |
| 4,146,732 A | 3/1979 | Padovan et al. |
| 4,147,885 A | 4/1979 | Shimizu et al. |
| 4,203,906 A | 5/1980 | Takada et al. |
| 4,256,783 A | 3/1981 | Takada et al. |
| 4,259,211 A | 3/1981 | Krabetz et al. |
| 4,317,926 A | 3/1982 | Sato et al. |
| 4,339,355 A | 7/1982 | Decker et al. |
| 4,365,087 A | 12/1982 | Kadowaki et al. |
| 4,873,368 A | 10/1989 | Kadowaki et al. |
| 5,177,260 A | 1/1993 | Kawajiri et al. |
| 5,218,146 A | 6/1993 | Takata et al. |
| 5,380,933 A | 1/1995 | Ushikubo et al. |
| 5,739,391 A | 4/1998 | Ruppel et al. |
| 5,821,390 A | 10/1998 | Ruppel et al. |
| 5,929,275 A | 7/1999 | Wada et al. |

FOREIGN PATENT DOCUMENTS

| EP | 0 700 893 | 3/1996 |
| EP | 0 911 313 | 4/1999 |
| WO | WO 00/53556 | 9/2000 |
| WO | WO 00/53557 | 9/2000 |
| WO | WO 00/53558 | 9/2000 |
| WO | WO 00/53559 | 9/2000 |

*Primary Examiner*—Johann Richter
*Assistant Examiner*—Paul A. Zucker
(74) *Attorney, Agent, or Firm*—Alan Holler; Kenneth Crimaldi

(57) ABSTRACT

This invention relates to a high load process for preparing (meth)acrylic acid from a reactive hydrocarbon using a high reactive hydrocarbon space velocity to provide increased capacity and throughput.

12 Claims, No Drawings

HIGH HYDROCARBON SPACE VELOCITY PROCESS FOR PREPARING UNSATURATED ALDEHYDES AND ACIDS

CROSS REFERENCE TO RELATED PATENT APPLICATIONS

This is a non-provisional application of prior pending U.S. provisional application Ser. No. 60/167,079 filed Nov. 23, 1999.

This invention relates to an improved process for preparing unsaturated aldehydes and acids utilizing high load reaction conditions. In particular, the invention relates to a process for preparing (meth)acrolein and/or (meth)acrylic acid from a reactive hydrocarbon utilizing a high reactive hydrocarbon space velocity thereby providing a process having increased capacity and throughput.

Unsaturated aldehydes and carboxylic acids are important commercial chemicals. Of particular importance are (meth) acrylic acid and (meth)acrolein. The highly reactive double bond and acid/aldehyde function of (meth)acrylic acid and (meth)acrolein make them especially suitable as a monomer or as a manufacturing feedstock which may be polymerized alone or with other monomers to produce commercially important polymers. These unsaturated acids/aldehydes are also useful as a starting material for esterification to produce commercially important (meth)acrylate esters or for producing other material using other reaction mechanisms. Such materials derived from (meth)acrylic acid or (meth)acrolein are useful as plastic sheets, parts, paints and other coatings, adhesives, caulks, sealants, and detergents as well as other applications.

The chemical reactions for the preparation of (meth) acrylic acid and/or (meth)acrolein are fairly well known. For instance, the preparation of acrylic acid from propylene generally proceeds in a vapor phase two step catalytic oxidation reaction. In the first step propylene is oxidized in the presence of oxygen, diluent inert gasses, water vapor, and appropriate catalysts to produce acrolein according to equation (I):

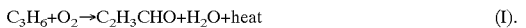

$$C_3H_6 + O_2 \rightarrow C_2H_3CHO + H_2O + \text{heat} \quad \text{(I).}$$

The acrolein is then oxidized, in a second step, in the presence of oxygen, diluent inert gasses, water vapor, and appropriate catalysts to form acrylic acid according to equation (II):

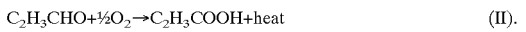

$$C_2H_3CHO + \tfrac{1}{2}O_2 \rightarrow C_2H_3COOH + \text{heat} \quad \text{(II).}$$

The two stage vapor phase catalytic oxidation of propylene to acrylic acid is generally performed using either tandem reactors wherein a separate reactor is utilized for each step or stage (e.g., see the description in U.S. Pat. No. 4,873,368) or by utilizing one reactor to perform both steps (e.g., see the description in U.S. Pat. No. 4,256,783). Furthermore, the acrolein may be prepared according to Equation (I) and then utilized as a feedstock for the preparation of various other materials.

The preparation of methacrolein and methacrylic acid from isobutylene proceeds in a similar manner.

It is known in the art that the productivity of such (meth)acrolein and/or (meth)acrylic acid manufacturing processes may be increased by feeding a higher concentration of the starting hydrocarbon to the reactor or by increasing the space velocity of the total reactant feed. For instance, see U.S. Pat. No. 5,929,275 which discloses a propylene space velocity of 128 hr$^{-1}$ in a process for making acrolein from propylene.

The reactive hydrocarbon space velocity, defined below, is a measure of the volume of reactive hydrocarbon which contacts a particular volume of catalyst per unit time. Consequently, when the concentration of the reactive hydrocarbon or the total space velocity is changed the reactive hydrocarbon. space velocity will change. For instance, when the reactive hydrocarbon concentration or the total space velocity is raised the reactive hydrocarbon space velocity will rise giving rise to higher load conditions.

However, attendant with such reaction conditions are several problems. For instance, in the preparation of acrolein and/or acrylic acid when propylene in the reactant composition is fed at high propylene concentrations or fed at higher space velocity, because each step of the two step oxidation of propylene to acrylic acid is highly exothermic, as the propylene concentration and/or space velocity get higher there is a danger that the reaction may proceed too quickly and become difficult to control. In extreme cases, catastrophic events may occur such as a runaway reaction.

Increased heat production from these reaction conditions also may lead to an increase in so-called hot spot formation and in an increase in the temperature maximum at a particular hot spot. Hot spots are maximums through which the reaction temperature of a particular reaction passes through as the reactants flow through the contact tube. Such hot spots can result in shortened catalyst life and impaired selectivity for the desired product.

Consequently, the oxidation of propylene to acrylic acid is generally practiced in the art utilizing a propylene concentration in the reactant gas feed composition of between 4 and 7 volume percent of the total reactant feed composition with a suitable space velocity. Typically, in the prior art, the reactive hydrocarbon space velocity is in a range of from 75 to 100 hr$^{-1}$. Generally, it is acknowledged in the art that such operating parameters will allow suitable safety with acceptable productivity and that operation outside these ranges is risky.

However, in the present day production of, for instance acrylic acid, it is a constant goal of manufacturers to gain the most productivity from manufacturing processes. It is thus a constant goal to be able to operate under high load conditions, i.e., greater than 100 hr$^{-1}$ reactive hydrocarbon space velocity to achieve such increased productivity.

U.S. Pat. No. 4,203,906 describes a single reactor system for preparing acrylic acid from propylene utilizing (see Example 5) a reactive hydrocarbon space velocity of 94.5 hr$^{-1}$.

U.S. Pat. Nos. 4,365,087 and 4,873,368 have dealt with the problem of increasing process productivity/capacity by raising the propylene concentration. However, the reactions were run with a higher contact time (lower space velocity) for the starting reactants. As a result the reaction was run at typical reactive hydrocarbon space velocities of about 85 to 90 hr$^{-1}$ (see for instance Example 1 of '087 and Examples 1–3 of '368).

U.S. Pat. No. 5,929,275 describes processes for the preparation of acrolein using reactive hydrocarbon space velocities from 100 to 128 hr$^{-1}$ (see the Examples). However, the control of hot spot formation under high load conditions is effected by controlling the amount of the catalytically active component to be loaded on an inactive carrier, the particle size of the catalyst, the particle size of the carrier and the calcining temperature of the catalyst-loaded carrier.

The present inventors have now discovered that high load conditions including increased reactant concentration and/or increased space velocity, heretofore thought unavailable, may be utilized in (meth)acrylic acid/(meth)acrolein manufacturing processes. Accordingly, a novel process for preparing (meth)acrylic acid and/or (meth)acrolein is described herein wherein the following advantages are provided:
(1) increased throughput/capacity is provided without additional capital expenditure;
(2) increased throughput/capacity is provided without unacceptable additional catalyst life reduction; and
(3) product yield loss is more than compensated for by higher throughput.

In one aspect of the present invention, there is provided a catalytic vapor phase oxidation process comprising (A) providing an oxidation reactor comprising a plurality of contact tubes disposed in a reactor shell, the inside of the reactor shell being divided into at least first and second heat transfer zones through each of which a heat transfer medium passes; each of said contact tubes containing at least two oxidation catalysts, said at least two oxidation catalysts being jointly capable of effecting the oxidation of a reactive hydrocarbon to a product gas comprising (meth)acrylic acid; said contact tubes containing at least two oxidation catalysts being packed with said at least two oxidation catalysts in such a manner so as to provide a peak-to-salt temperature sensitivity of not more than 9° C.; and (B) feeding a reactant composition comprising (i) at least one reactive hydrocarbon and (ii) oxygen into said oxidation reactor, at a reactive hydrocarbon space velocity of from 135 $hr^{-1}$ to 300 $hr_{-1}$, to contact said composition with said at least two oxidation catalysts to form a product gas comprising (meth)acrylic acid.

In a second aspect of the present invention, there is provided a catalytic vapor phase oxidation process, comprising: (A) providing a first oxidation reactor comprising a plurality of contact tubes disposed in a reactor shell, the inside of the reactor shell being divided into at least a first heat transfer zone through each of which a heat transfer medium passes; each of said contact tubes containing at least one first oxidation catalyst, said at least one first oxidation catalyst being capable of effecting the oxidation of a first reactive hydrocarbon and oxygen to a first product gas comprising at least one second reactive hydrocarbon and oxygen, said contact tubes containing at least one first oxidation catalyst being packed in such a manner so as to provide a peak-to-salt temperature sensitivity of not more than 9° C.; (B) feeding said first reactant composition comprising (i) at least one first reactive hydrocarbon and (ii) oxygen into said first oxidation reactor, at a first reactive hydrocarbon space velocity of from 135 $hr^{-1}$ to 300 $hr^{-1}$, to contact said first reactant composition with said at least one first oxidation catalyst to form a first product gas comprising at least one second reactive hydrocarbon and oxygen; (C) providing a second oxidation reactor comprising a plurality of contact tubes disposed in a reactor shell, the inside of the reactor shell being divided into at least a first heat transfer zone through each of which a heat transfer medium passes; each of said contact tubes containing at least one second oxidation catalyst, said at least one second oxidation catalyst being capable of effecting the oxidation of said second reactive hydrocarbon and oxygen to a final product gas comprising (meth)acrylic acid, said contact tubes containing said at least one second oxidation catalyst being packed with said at least one second catalyst in such a manner so as to provide a Δ-peak value of not more than 5° C.; (D) feeding said first product gas comprising (i) at least one second reactive hydrocarbon and (ii) oxygen into said second oxidation reactor, at a second reactive hydrocarbon space velocity of from 135 $hr^{-1}$ to 300 $hr^{-1}$; to contact said first product gas with said at least one second oxidation catalyst to form a final product gas comprising (meth)acrylic acid.

In a third aspect of the present invention, there is provided a catalytic vapor phase oxidation process, comprising: (A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising at least one reactive hydrocarbon selected from the group consisting of acrolein, methacrolein and mixtures thereof and oxygen into a product gas comprising (meth)acrylic acid, said contact tubes containing at least one oxidation catalyst being packed with said at least one oxidation catalyst in such a manner so as to provide a peak-to-salt temperature sensitivity of not more than 9° C.; (B) feeding a reactant composition comprising (i) at least one reactive hydrocarbon selected from the group consisting of acrolein, methacrolein and mixtures thereof, and (ii) oxygen into said oxidation reactor, at a reactive hydrocarbon space velocity of from 135 $hr^{-1}$ to 300 $hr^{-1}$, to contact said reactant composition with said at least one oxidation catalyst to form a product gas comprising (meth)acrylic acid.

In a fourth aspect of the present invention, there is provided a catalytic vapor phase oxidation process, comprising: (A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising at least one reactive hydrocarbon selected from the group consisting of propylene, isobutylene and mixtures thereof and oxygen into a product gas comprising (meth)acrolein, said contact tubes containing said at least one oxidation catalyst being packed with said at least one oxidation catalyst in such a manner so as to provide a peak-to-salt temperature sensitivity of not more than 9° C.; (B) feeding a reactant composition comprising (i) at least one reactive hydrocarbon selected from the group consisting of propylene, isobutylene and mixtures thereof and (ii) oxygen into said oxidation reactor, at a reactive hydrocarbon space velocity of from 135 $hr^{-1}$ to 300 $hr^{-1}$, to contact said reactant composition with said at least one oxidation catalyst to form a product gas comprising (meth)acrolein.

In a fifth aspect of the present invention, there is provided a catalytic vapor phase oxidation process, comprising:
(A) providing an oxidation reactor comprising a plurality of contact tubes disposed in a reactor shell, the inside of the reactor shell being divided into at least first and second heat transfer zones through each of which a heat transfer medium passes; each of said contact tubes containing at least two sequentially disposed oxidation catalysts, said at least two oxidation catalysts being jointly capable of effecting the oxidation of a reactive hydrocarbon to a product gas comprising (meth)acrylic acid, a first oxidation catalyst in said sequence being capable of effecting the oxidation of a reactive hydrocarbon to (meth)acrolein and being substantially located in that portion of each contact tube in contact with the first heat transfer zone, a second oxidation catalyst in said sequence being capable of effecting the oxidation of (meth)acrolein to (meth)acrylic acid and being substantially located in that portion of each contact tube in contact with the second heat transfer zone; said contact tubes containing said at least two oxidation catalysts being packed with said at least two oxidation catalysts in such a manner so as to provide a peak-to-salt temperature sensitivity of not more than 9° C.; and (B) feeding a reactant composition comprising
   (i) at least one reactive hydrocarbon,
   (ii) oxygen,
   (iii) less than 15% by. volume of the reactant composition of carbon oxides, and
   (iv) less than 15% by volume of the reactant composition of inert gas fuel,
      with the proviso that the combined amount of carbon oxides and inert gas fuel present in the reactant composition is less than 15% by volume of the reactant composition, into said oxidation reactor, at a reactive hydrocarbon space velocity of from 135 hr$^{-1}$ to 300 hr$^{-1}$, to contact said reactant composition with said at least two oxidation catalysts to form a product gas comprising (meth)acrylic acid;

wherein, when said portion of each contact tube in contact with the first heat transfer zone comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is less than +5° C.;

wherein, when said portion of each contact tube in contact with the second heat transfer zone comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

In a sixth aspect of the present invention, there is provided a catalytic vapor phase oxidation process, comprising:

(A) providing a first oxidation reactor comprising a plurality of contact tubes disposed in a reactor shell, the inside of the reactor shell being divided into at least a first heat transfer zone through each of which a heat transfer medium passes; each of said contact tubes containing at least one first oxidation catalyst, said at least one first oxidation catalyst being capable of effecting the oxidation of a first reactive hydrocarbon and oxygen to a first product gas comprising at least one second reactive hydrocarbon and oxygen, said contact tubes containing at least one first oxidation catalyst being packed in such a manner so as to provide a peak-to-salt temperature sensitivity of not more than 9° C.;

(B) feeding said first reactant composition comprising
   (i) at least one first reactive hydrocarbon, and
   (ii) oxygen,
   (iii) less than 15% by volume of the reactant composition of carbon oxides, and
   (iv) less than 15% by volume of the reactant composition of inert gas fuel,
      with the proviso that the combined amount of carbon oxides and inert gas fuel present in the reactant composition is less than 15% by volume of the reactant composition, into said first oxidation reactor, at a first reactive hydrocarbon space velocity of from 135 hr$^{-1}$ to 300 hr$^{-1}$, to contact said first reactant composition with at least one first oxidation catalyst to form a first product gas comprising at least one second reactive hydrocarbon and oxygen;

wherein, when each said contact tube of said first oxidation reactor comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is less than +5° C.;

(C) providing a second oxidation reactor comprising a plurality of contact tubes disposed in a reactor shell, the inside of the reactor shell being divided into at least a first heat transfer zone through each of which a heat transfer medium passes; each of said contact tubes containing at least one second oxidation catalyst, said at least one second oxidation catalyst being capable of effecting the oxidation of said second reactive hydrocarbon and oxygen to a final product gas comprising (meth)acrylic acid, said contact tubes containing at least one second oxidation catalyst being packed with said at least one second catalyst in such a manner so as to provide a peak-to-salt temperature sensitivity of not more than 9° C.;

(D) feeding said first product gas comprising
   (i) at least one second reactive hydrocarbon, and
   (ii) oxygen into said second oxidation reactor, at a second reactive hydrocarbon space velocity of from 135 hr$^{-1}$ to 300 hr$^{-1}$; to contact said first product gas with said at least one second oxidation catalyst to form a final product gas comprising (meth)acrylic acid;

wherein, when each said contact tube of said second oxidation reactor comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

In a seventh aspect of the present invention, there is provided a catalytic vapor phase oxidation process, comprising:

(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising at least one reactive hydrocarbon selected from the group consisting of acrolein, methacrolein, and mixtures thereof and oxygen into a product gas comprising (meth)acrylic acid, said contact tubes containing at least one oxidation catalyst being packed with said at least one oxidation catalyst in such a manner so as to provide a peak-to-salt temperature sensitivity of not more than 9° C.;

(B) feeding a reactant composition comprising
   (i) at least one reactive hydrocarbon selected from the group consisting of acrolein, methacrolein, and mixtures thereof,
   (ii) oxygen,
   (iii) less than 15% by volume of the reactant composition of carbon oxides, and
   (iv) less than 15% by volume of the reactant composition of inert gas fuel,
      with the proviso that the combined amount of carbon oxides and inert gas fuel present in the reactant composition is less than 15% by volume of the reactant composition, into said oxidation reactor, at a reactive hydrocarbon space velocity of from 135 hr$^{-1}$ to 300 hr$^{-1}$, to contact said reactant composition with said at least one oxidation catalyst to form a product gas comprising (meth)acrylic acid;

wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is less than +5° C.

In an eighth aspect of the present invention, there is provided a catalytic vapor phase oxidation process, comprising:

(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising: at least one reactive hydrocarbon selected from the group consisting of propylene, isobutylene, and mixtures thereof and oxygen into a product gas comprising (meth)acrolein, said contact tubes containing at least one oxidation catalyst being packed with said at least one oxidation catalyst in such a manner so as to provide a peak-to-salt temperature sensitivity of not more than 9° C.;

(B) feeding a reactant composition comprising
    (i) at least one reactive hydrocarbon selected from the group consisting of propylene, isobutylene, and mixtures thereof, and
    (ii) oxygen,
    (iii) less than 15% by volume of the reactant composition of carbon oxides, and
    (iv) less than 15% by volume of the reactant composition of inert gas fuel,
        with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$ to contact said reactant composition with said at least one oxidation catalyst to form a product gas comprising (meth)acrolein;

wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is less than +5° C.

In a ninth aspect of the present invention, there is provided a catalytic vapor phase oxidation process, comprising:

(A) providing an oxidation reactor comprising a plurality of contact tubes disposed in a reactor shell, the inside of the reactor shell being divided into at least first and second heat transfer zones through each of which a heat transfer medium passes; each of said contact tubes containing at least two sequentially disposed oxidation catalysts, said at least two oxidation catalysts being jointly capable of effecting the oxidation of a reactive hydrocarbon to a product gas comprising (meth)acrylic acid, a first oxidation catalyst in said sequence being capable of effecting the oxidation of a reactive hydrocarbon to (meth)acrolein and being substantially located in that portion of each contact tube in contact with the first heat transfer zone, a second oxidation catalyst in said sequence being capable of effecting the oxidation of (meth)acrolein to (meth)acrylic acid and being substantially located in that portion of each contact tube in contact with the second heat transfer zone; said contact tubes containing said at least two oxidation catalysts being packed with said at least two oxidation catalysts in such a manner so as to provide a peak-to-salt temperature sensitivity of not more than 9° C.; and (B) feeding a reactant composition comprising
    (i) at least one reactive hydrocarbon,
    (ii) oxygen,
    (iii) less than 15% by volume of the reactant composition of carbon oxides, and
    (iv) less than 15% by volume of the reactant composition of inert gas fuel,
        with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$, to contact said reactant composition with said at least two oxidation catalysts to form a product gas comprising (meth)acrylic acid;

wherein, when said portion of each contact tube in contact with the first heat transfer zone comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is greater than +5° C.;

wherein, when said portion of each contact tube in contact with the second heat transfer zone comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

In a tenth aspect of the present invention, there is provided a catalytic vapor phase oxidation process, comprising:

(A) providing a first oxidation reactor comprising a plurality of contact tubes disposed in a reactor shell, the inside of the reactor shell being divided into at least a first heat transfer zone through each of which a heat transfer medium passes; each of said contact tubes containing at least one first oxidation catalyst, said at least one first oxidation catalyst being capable of effecting the oxidation of a first reactive hydrocarbon and oxygen to a first product gas comprising at least one second reactive hydrocarbon and oxygen, said contact tubes containing at least one first oxidation catalyst being packed in such a manner so as to provide a peak-to-salt temperature sensitivity of not more than 9° C.;

(B) feeding said first reactant composition comprising
    (i) at least one first reactive hydrocarbon, and
    (ii) oxygen,
    (iii) less than 15% by volume of the reactant composition of carbon oxides, and
    (iv) less than 15% by volume of the reactant composition of inert gas fuel,
        with the proviso that the combined amount of carbon oxides and inert gas fuel present in the reactant composition is less than 15% by volume of the reactant composition,
into said first oxidation reactor, at a first reactive hydrocarbon space velocity of from 135 hr$^{-1}$ to 300 hr$^{-1}$, to contact said first reactant composition with at least one first oxidation catalyst to form a first product gas comprising at least one second reactive hydrocarbon, oxygen, carbon oxides and inert gas fuel;

wherein, when each said contact tube of said first oxidation reactor comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is greater than +5° C.;

(C) providing a second oxidation reactor comprising a plurality of contact tubes disposed in a reactor shell, the inside of the reactor shell being divided into at least a first heat transfer zone through each of which a heat transfer medium passes; each of said contact tubes containing at least one second oxidation catalyst, said at least one second oxidation catalyst being capable of effecting the oxidation of said second reactive hydrocarbon and oxygen to a final product gas comprising (meth)acrylic acid, said contact tubes containing at least one second oxidation catalyst being packed with said at least one second catalyst in such a manner so as to provide a peak-to-salt temperature sensitivity of not more than 9° C.;

(D) feeding said first product gas comprising
  (i) at least one second reactive hydrocarbon,
  (ii) oxygen,
  (iii) carbon oxides, and
  (iv) inert gas fuel
into said second oxidation reactor, at a second reactive hydrocarbon space velocity of from 135 hr$^{-1}$ to 300 hr$^{-1}$; to contact said first product gas with said at least one second oxidation catalyst to form a final product gas comprising (meth)acrylic acid;

wherein, when each said contact tube of said second oxidation reactor comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is greater than +5° C.

In an eleventh aspect of the present invention, there is provided a catalytic vapor phase oxidation process, comprising:

(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising at least one reactive hydrocarbon selected from the group consisting of acrolein, methacrolein, and mixtures thereof and oxygen into a product gas comprising (meth)acrylic acid, said contact tubes containing at least one oxidation catalyst being packed with said at least one oxidation catalyst in such a manner so as to provide a peak-to-salt temperature sensitivity of not more than 9° C.;

(B) feeding a reactant composition comprising
  (i) at least one reactive hydrocarbon selected from the group consisting of acrolein, methacrolein, and mixtures thereof,
  (ii) oxygen,
  (iii) less than 15% by volume of the reactant composition of carbon oxides, and
  (iv) less than 15% by volume of the reactant composition of inert gas fuel,
    with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$, to contact said reactant composition with said at least one oxidation catalyst to form a product gas comprising (meth)acrylic acid;

wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is greater than +5° C.

In a twelfth aspect of the present invention, there is provided a catalytic vapor phase oxidation process, comprising:

(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising: at least one reactive hydrocarbon selected from the group consisting of propylene, isobutylene, and mixtures thereof and oxygen into a product gas comprising (meth)acrolein, said contact tubes containing at least one oxidation catalyst being packed with said at least one oxidation catalyst in such a manner so as to provide a peak-to-salt temperature sensitivity of not more than 9° C.;

(B) feeding a reactant composition comprising
  (i) at least one reactive hydrocarbon selected from the group consisting of propylene, isobutylene, and mixtures thereof,
  (ii) oxygen,
  (iii) less than 15% by volume of the reactant composition of carbon oxides, and
  (iv) less than 15% by volume of the reactant composition of inert gas fuel,
    with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$ to contact said reactant composition with said at least one oxidation catalyst to form a product gas comprising (meth)acrolein;

wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is greater than +5° C.

Throughout this specification and claims, unless otherwise indicated, references to percentages are by molar volume and all temperatures are in degree centigrade.

It is also to be understood that for purposes of this specification and claims that the range and ratio limits, recited herein, are combinable. For example, if ranges of 1–20 and 5–15 are recited for a particular parameter, it is understood that ranges of 1–15 or 5–20 are also contemplated.

Throughout this specification and claims the terms "water vapor" and "steam" are understood to be synonymous.

The term "inert" as used herein is meant to indicate that the particular material does not participate in, is unaffected by, and/or is otherwise inactive in the (meth)acrylic acid reaction system disclosed herein. Accordingly, a material such as propane is easily reacted or combusted in other systems, but in the reaction system of the present invention is considered inert.

The term "catalyst" as used herein refers to pure catalysts, or pure catalyst provided on a support, by coating, impregnating etc., such pure catalyst on a support material. Accordingly, the terminology 100 percent catalyst refers not only to a material which is pure catalyst, but to 100 percent of a material which includes catalyst on a support material and/or impurities when purchased. That is, 100 percent catalyst refers to 100 percent of the catalyst as purchased, whether it be as neat chemical or with a support material.

The term "(meth)acrylic acid" as used herein refers to both methacrylic acid and acrylic acid and in a like manner the term "(meth)acrolein" refers to both methacrolein and acrolein.

The term "space velocity" or "SV" as used herein= (volumetric flow rate of the starting gas at STP/reactor volume(unpacked)). The term "residence time" as used herein=1/SV.

The term "reactive hydrocarbon space velocity" as used herein=(SV)×(the reactive hydrocarbon feed concentration).

The propylene conversion=(# moles propylene converted/# of moles propylene employed)×100.

The acrylic acid selectivity=(# of moles of acrylic acid produced/# of moles propylene converted)×100.

The acrolein selectivity=(# of moles of acrolein produced/# of moles propylene converted)×100.

The acrylic acid yield=(# of moles acrylic acid produced/# of moles propylene employed)×100.

The term "reactive hydrocarbon", as used herein, includes pure and substituted hydrocarbons as well as unsaturated hydrocarbons and hydrocarbon derivatives.

Although the invention is generally described below in regard to the preparation of acrolein and/or acrylic acid, it will be understood by those skilled in the art that the invention is applicable to the preparation of other unsaturated aldehydes and acids, including methacrolein and methacrylic acid.

As recited above, the catalytic vapor phase process of the present invention includes feeding a reactant composition into an oxidation reactor. The reactant composition includes at least one reactive hydrocarbon and an oxygen-containing material.

In one embodiment, the reactive hydrocarbon is an unsaturated hydrocarbon including, but not limited to, propylene, isobutylene and mixtures thereof. In a preferred embodiment, the reactive hydrocarbon is propylene. The propylene used may be from any source and may be any grade suitable for an acrolein and/or acrylic acid producing vapor phase oxidation reaction. Suitable grades include, but are not limited to, polymer grade (generally greater than or equal to 99% propylene), chemical grade (generally greater than or equal to 94% propylene), and refinery grade (generally greater than or equal to 60% propylene). In a more preferred embodiment, the propylene content is greater than or equal to 94% propylene. Use of chemical grade or refinery grade propylene has the added advantage of providing combustible materials such as propane which are present as impurities. The propane provides more inert gas to the system, but more importantly provides fuel for the thermal or catalytic oxidation or incineration of absorber off-gas. Accordingly, the propane impurity enters the thermal or catalytic oxidizer or incinerator with the absorber off-gas and reduces the additional fuel required to burn the off-gas. Generally, chemical grade propylene contains up to 6 percent combustible impurities and refinery grade propylene contains up to 40 percent combustible impurities.

If propylene is utilized it is generally present in the reactant composition at greater than 7 percent by volume of the reactant composition. However, it will be understood by those skilled in the art that high load conditions, that is the reactive hydrocarbon space velocities of the present invention, may be obtained by decreasing the concentration of the propylene and increasing the total space velocity.

Typically, the reactive hydrocarbon is present in the reactant composition at a range from 1 to 20 volume percent. In one embodiment, the reactive hydrocarbon is propylene, and is present at a range of from 4 to 11. In an alternative embodiment, the reactive hydrocarbon is present at a range of 7 to 11, preferably 7.5 to 9 percent by volume of the reactant composition. In another embodiment, the reactive hydrocarbon is a hydrocarbon derivative including, but not limited to, acrolein, methacrolein and mixtures thereof In an alternative embodiment, the reactive hydrocarbon is acrolein. The acrolein used may be from any source and may be any grade suitable for an acrylic acid producing vapor phase oxidation reaction. Typically the acrolein is generated and supplied utilizing the first stage reaction for the production of acrylic acid described above. The acrolein may be produced in situ in the first stage of a single reactor system and be introduced into the second stage of the single reactor system for conversion to acrylic acid. Alternatively, the acrolein may be generated in a first oxidation reactor of a tandem reactor system and then passed into a second oxidation reactor as part of the second reactant composition for conversion into acrylic acid. Acrolein is generally present in the reactant composition at a range from 1 to 22 percent by volume of the reactant composition. In one embodiment, acrolein is present at a range of from 5 to 18, preferably, 6 to 12 percent by volume of the reactant composition.

Typically, the reactive hydrocarbon is fed to a single reactor system reactor at a reactive hydrocarbon space velocity of 135 to 300 hr$^{-1}$, preferably 135 to 250 hr$^{-1}$, more preferably 140 to 230 hr$^{-1}$. Alternatively, the reactive hydrocarbon is fed to the first oxidation reactor of a tandem reactor system of at a reactive hydrocarbon space velocity of 135 to 300 hr$^{-1}$, preferably 135 to 250 hr$^{-1}$, more preferably 135 to 225 hr$^{-1}$ and then on to the second oxidation reactor of the tandem system at a reactive hydrocarbon space velocity of 135 to 300 hr$^{-1}$, preferably 135 to 250 hr$^{-1}$, more preferably 135 to 225 hr$^{-1}$. It is to be understood that in the tandem reactor situation the initial reactive hydrocarbon space velocity to the second oxidation reactor is calculated from the initial reactant feed, including the propylene concentration and the reactor volume (unpacked) of the second oxidation reactor catalyst.

The oxygen containing material in the reaction composition may be any material containing an amount of oxygen sufficient to maintain the oxidation reactions of the present invention. Suitable examples include, without limitation, air, oxygen-enriched air, pure oxygen, and mixtures of pure oxygen and at least one inert gas or mixtures thereof. The preferred source of oxygen is air. Typically oxygen is present in the reactant composition in an amount suitable to meet the stoichiometric needs of the reaction. Generally, an amount of oxygen which will provide an oxygen/propylene ratio in the reactant composition of 1.6 to 2.2:1.0, preferably 1.6 to 2.0:1.0, is provided.

The reactant composition(s) may also contain water vapor which may be present in the reaction composition in an amount of 2 to 30, preferably 5 to 11 percent by volume of the reactant composition. Alternatively, in the absence of recycle, the water vapor may be present at a range from 15 to 25 percent by volume of the reactant composition. The water vapor may be provided by recycle from other process steps or be otherwise generated and provided to the reactant composition or may be provided by both recycle and generation.

In a preferred embodiment, water vapor is at least in part provided by recycle of the absorber off-gas back to the reactor. The acrylic acid prepared according to the present invention is present in a mixed product gas exiting the single reactor system reactor or second oxidation reactor of a tandem system. Generally, the mixed product gas is cooled and is contacted with an aqueous stream in an absorption tower, thereby providing an aqueous acrylic acid solution from which acrylic acid can be isolated and purified. The remainder of the product gasses, known as the absorber waste gas or absorber off-gas, is typically incinerated or undergoes waste treatment. Depending on the reactants feed gas composition, the absorber off-gas may contain inert gasses, $O_2$, water vapor, CO, $CO_2$, unreacted propylene, unreacted acrolein and/or acrylic acid.

Inert gas may also be used in the reaction composition and may be any gaseous material or mixtures of gaseous materials which is inert to the oxidation reactions of the present invention. Typical examples include, but are not limited to, nitrogen, carbon dioxide, helium, argon, propane and carbon monoxide, or mixtures thereof. The preferred inert gas is nitrogen or a mixture of nitrogen with at least one other inert gas. The preferred source of nitrogen is at least one of air, recycled absorber off-gas, recycled stack gas, and mixtures thereof The inert gas generally constitutes a major amount of the remainder of the reactant composition which is not propylene, oxygen, or water vapor. Generally, the inert gas is 50 to 99.9, preferably 60 to 99.9 volume percent of the remainder of the reactant composition.

It is known in the art to recycle at least a portion of the absorber off-gas back to the reactor(s) to provide inert diluent gas and steam to the reactant composition. Recycle of the absorber off-gas can be used to provide at least a portion of the necessary diluent gasses and steam to the reactor feed to assure a suitable reactive hydrocarbon and water vapor concentration. In addition, recycling the absorber off-gas serves to reduce waste water generated by the process by reducing the amount of steam that is fed to the process. Furthermore, small amounts of unreacted propylene and/or acrolein contained in the off-gas are given another chance to react and thereby improve the overall acrylic acid yield by optimizing conversions of propylene and acrolein.

In an alternative preferred embodiment, all of the absorber off-gas is added to the thermal or catalytic oxidizer/incinerator feed and is burned. At least a portion of the stack gas from the thermal or catalytic oxidizer generated during operation is then recycled back to the oxidation reactor(s). Generally, the recycle of the absorber off-gas or the recycle of the stack case is limited to the case where the amount of carbon oxides (CO and/or $CO_2$) is less than 15 volume percent of the reactant composition, preferably less than 10 volume percent of the reactant composition.

As recited above, the reaction composition may optionally include at least one inert gas which is suitable for use as fuel for thermal or catalytic oxidation/incineration of waste absorber off-gas. Such inert gas fuel may be provided as part of the impurities in the propylene feed, as part of the absorber off-gas, or as neat chemical. Suitable examples include, but are not limited to, propane, ethane, methane, butane, pentane or mixtures of one or more of the above. In one embodiment, the inert gas fuel is propane. Generally, such inert gas fuel is present in a minor amount in the reactant composition, for example, the inert gas fuel is less than 15 volume percent of the reactant composition, preferably less than 10 volume percent of the reactant composition. When carbon oxides (CO and/or $CO_2$) and inert gas fuel are present in the reactant composition, the combined amount thereof should be less than 15 volume percent of the reactant composition, preferably less than 10 volume percent of the reactant composition.

In a preferred embodiment, the water vapor and inert gas and optionally at least a portion of the inert gas fuel, of the reaction composition, are provided by recycle of the absorber off-gas to the reactor. Generally, an amount of absorber off-gas is recycled which is suitable to provide the appropriate amounts of water vapor and inert gas. However, it is understood by those skilled in the art that the absorber off-gas may not provide all of the requirements of water vapor and/or inert gas of the system and additional amounts may be added from other sources. When absorber off-gas recycle is not used, steam and nitrogen are used as the primary diluents. Steam is not consumed, but may alter the selectivity, conversion and/or catalytic activity in the oxidation reactions and is part of the mixed product gasses emerging from the reactor. When the mixed product gasses are introduced into the absorption column, the steam substantially condenses at the bottom of the absorption column and is a small part of the gasses flowing through the absorber.

The oxidation reactor may be any oxidation reactor suitable for the, manufacture of an unsaturated aldehyde or acid. Preferably, the oxidation reactor is a shell and multiple contact tube heat exchange reactor. Generally, such a reactor includes a plurality of catalytic contact tubes disposed in a shell through which at least one heat exchange medium passes.

In one embodiment, the oxidation reactor may be a single reactor system which is a shell and multiple contact tube heat exchange reactor having a plurality of catalytic contact tubes disposed in a shell through which at least two heat exchange medium circuits pass. Specifically, the inside of the reactor shell is divided into at least a first heat transfer zone and a second heat transfer zone through each of which a heat transfer medium passes. The catalytic contact tubes run longitudinally from the top portion to the bottom portion of the reactor through a perforated tubesheet. It is understood that the reactor may contain one or more perforated tubesheets which divide the reactor into two or more heat transfer zones. Suitable single reactor systems are described, for instance in U.S. Pat. Nos. 4,256,783; 4,203,906; 5,151,605; and co-pending U.S. Pat. application Ser. No. 09/244,182 which are incorporated herein by reference to the extent they teach a single reactor system.

Such a single reactor system provides the ability to run an oxidation reaction at several temperatures or to run several oxidation reactions, each at a different temperature, in a single reactor. A single reactor system may be utilized, for instance, when different temperature zones are required or desired in a vapor phase oxidation reaction. For example, a single reactor system may be utilized in the two step oxidation of propylene to acrylic acid, wherein in a first stage propylene is oxidized to acrolein at a particular temperature range, which in turn passes to the second stage and is oxidized at a different temperature range to acrylic acid. Each of said stages may be further divided into a plurality (i.e. two or more) of sequential reaction zones, each of which may be maintained at a desired temperature. Typically, the temperature of each subsequent reaction zone in a stage is less than 5° C. higher than, preferably less than, the temperature of the immediately preceding reaction zone in the stage. However, in some instances, the temperature of each subsequent reaction zone in a stage may be greater than 5° C. higher than, preferably greater than 10° C. higher than, the temperature of the immediately preceding reaction zone in the stage. Typically, each stage may be divided into two sequential reaction zones.

In an alternative embodiment, the oxidation reactor may be a single reactor wherein the reactor is maintained at one temperature range. Specifically, the oxidation reactor may be a shell and multiple contact tube heat exchange reactor having a plurality of catalytic contact tubes disposed in a shell through which one heat exchange medium circuit passes. Alternatively, it will be recognized by those skilled in the art that the reactor may also be maintained at two or more temperature ranges, as noted above, and that two or more heat exchange circuits may be utilized.

Such a reactor is useful in a so called tandem reactor system wherein two reactors are utilized, one for each stage, in the two step oxidation of propylene to acrylic acid. In such a system the first reactor is utilized to produce acrolein which is then passed through an interstage cooler and on to a second reactor wherein the acrolein is oxidized to acrylic acid. Of course, it will be recognized by one skilled in the art that it is not necessary that such a reactor be operated in tandem with another reactor. Rather, the reactor may stand alone to produce an unsaturated aldehyde or acid. Such a reactor is described, for instance in U.S. Pat. Nos. 5,739,391 and 5,821,390 which are incorporated by reference to the extent they teach reactors maintained at a single temperature range.

Any catalysts suitable for the vapor phase catalytic oxidation of a reactive hydrocarbon to an unsaturated aldehyde or acid may be used in the process of the present invention. Such catalysts are known and used in the art. For example, suitable catalysts for the oxidation of propylene to acrolein (hereinafter referred to as R1 catalysts) are described in, for instance, U.S. Pat. Nos. 4,025,565; 5,821,390; and 5,929,275. Suitable catalysts for the oxidation of acrolein to acrylic acid (hereinafter referred to as R2 catalysts) are described in, for instance, U.S. Pat. Nos. 3,775,474; 3,893,951; 3,954,855; 4,075,127; 4,146,732; 4,259,211; 4,339,355; 5,177,260; and 5,739,391. Suitable catalysts for the oxidation of propane to acrylic acid are described in, for instance, U.S. Pat. No. 5,380,933; and co-pending U.S. Patent Application Ser. No. 09/316,007.

The catalyst may be packed into the catalyst contact tube in any suitable manner. In one embodiment, each of the catalyst contact tubes includes one or more catalysts which individually or in combination are capable of effecting the preparation of acrylic acid from acrolein or acrolein from propylene. In a further embodiment, each of the contact tubes includes reaction zones A and A' each containing one or more catalysts which individually or in combination are capable of effecting the oxidation of propylene to acrolein. In one embodiment, reaction zones A and A' have a different catalytic activity for converting propylene to acrolein or for converting acrolein to acrylic acid. Such differing activity may be achieved by reaction zones A and A' having diluted or undiluted catalyst as well as differing dilutions respectively, by containing different catalyst having differing activity, or by being controlled to differing temperatures, as noted above.

In an alternative embodiment, each of the contact tubes contains at least two catalysts at least capable of catalyzing oxidation of propylene to acrolein and at least capable of catalyzing oxidation of acrolein to acrylic acid. The at least two catalysts may be packed so as to overlap or be intertwined or be disposed within the contact tubes sequentially so that the reactants contact a first catalyst capable of effecting the oxidation of propylene to acrolein and then a second catalyst capable of effecting the oxidation of acrolein to acrylic acid.

In an alternative embodiment, each of the contact tubes include at least two catalysts at least capable of catalyzing oxidation of propylene to acrolein and at least capable of catalyzing the oxidation of acrolein to acrylic acid. In one embodiment, each of the contact tubes contain reaction zones A and A' which contain one or more catalysts at least capable of catalyzing oxidation of propylene to acrolein and reaction zones B and B' which contain one or more catalysts at least capable of catalyzing oxidation of acrolein to acrylic acid. In one embodiment, reaction zones A and A' have a different catalytic activity for converting propylene into acrolein and/or reaction zones B and B' have a different activity for converting acrolein to acrylic acid. As discussed above, such differing activity may be achieved by catalyst dilution, by using different catalyst having different activity, or by temperature control.

In another embodiment, the two previous embodiments may be combined so that each contact tube may have reaction zones A, A' and B; A, A', and B'; A, B, and B'; or A', B, and B'.

In a further embodiment, a reaction zone A" containing 0 to 10 percent by weight catalyst is disposed between the A reaction zones, e.g., A or A', and the B reaction zones, e.g., B or B', in each contact tube. Generally, zone A" is less than 10 percent of the total length of the contact tube. For instance in one embodiment zone A" is 350 to 850, preferably 380 to 650 mm long. In one embodiment, the reaction zone A" is packed with a high surface area material with a heat transfer enhancing shape which is inert to and stable in the reaction system. Suitable examples include, alumina, alundum, mullite, carborundum, steel including stainless steel, copper, aluminum and ceramics. Furthermore, as stated above the material should be in a form in which its outer surface area is large including, without limitation, small spheres, cylinders, rings, filament, meshes and ribbons. In another embodiment, reaction zone A" contains from 0.1 to 5 percent by weight of at least one catalyst capable of effecting the oxidation of propylene to acrolein and/or the oxidation of acrolein to acrylic acid.

In an alternative embodiment, tandem reactors are used whereby the first stage reactor includes a reaction zone A which contains one or more catalysts at least capable of catalyzing oxidation of propylene to acrolein and the second stage tandem reactor includes a reaction zone B which contain one or more catalysts at least capable of catalyzing oxidation of acrolein to acrylic acid. In a preferred embodiment, tandem reactors are used whereby the first stage reactor includes reaction zones A and A' which contain one or more catalysts at least capable of catalyzing oxidation of propylene to acrolein and the second stage tandem reactor includes reaction zones B and B' which contain one or more catalysts at least capable of catalyzing oxidation of acrolein to acrylic acid. In one embodiment, reaction zones A and A' have a different catalytic activity for converting propylene into acrolein and/or reaction zones B and B' have a different activity for converting acrolein to acrylic acid. As recited above, several means are available for achieving differing catalytic activities.

Optionally, as described above each reactor, i.e., the first and second oxidation reactors may have an additional reaction zone A" or B" which may be located before zone A (or B), between zones A and A' (or between B and B'), or after A' (or B'). Such reaction zone is as described above.

Regardless of the manner that the catalyst(s) is packed into the contact tubes, the packing must be effected in such a manner so as to provide a peak-to-salt temperature sensitivity of not more than 9° C., preferably not more than 6° C., most preferably not more than 3° C. The peak-to-salt temperature sensitivity is the increase in catalyst peak temperature measured in ° C., brought about by increasing the heat transfer medium temperature by 1° C. The peak-to-salt temperature sensitivity may be empirically determined by packing a single tube as would be utilized in the oxidation reactor (i.e., same tube size (inside diameter and outside diameter) and cross-section, same material of construction, same length), in the same manner as contemplated for use in the oxidation reactor (using or not using zones such as A, A', A", B, B' and B", etc., having the zone(s) of the same length as contemplated for actual reactor operation, having the zone(s) contain the same catalyst(s) as contemplated for actual use) and fitted out with heat transfer zone(s) as contemplated for use in the actual oxidation reactor. Then, using the desired reactive hydrocarbon space velocity, under reaction conditions to produce 94–99% propylene conversion, preferably 95–99% propylene conversion, or 97–99.9% acrolein conversion, preferably 98–99.9% acrolein conversion, the peak-to-salt temperature sensitivity is determined by raising the temperature of the heat transfer media and determining the increase of the catalyst peak temperature. Conversion levels can be monitored by the use of on-line gas chromatographic analysis of both the feed and effluent compositions.

Typically, the oxidation reactor will contain greater than 5,000 catalyst contact tubes. In one embodiment, the oxidation reactor contains greater than 15,000 catalyst contact tubes. In another embodiment, the reactor contains greater than 20,000, preferably greater than 25,000 catalyst contact tubes. In an alternative embodiment, the reactor contains greater than 30,000 catalyst contact tubes. The contact tubes utilized are those generally known and used in the art. The contact tubes may be arranged in any suitable arrangement known in the art. Such suitable arrangements are described and disclosed in, for instance, U.S. Pat. Nos. 4,256,783; 5,161,605; and DE 2,201,528.

As recited above, the oxidation reactor, whether it is a single reactor system or simply a single reactor of a tandem system, may be divided into a first heat transfer zone and a second heat transfer zone by a perforated tubesheet through which the contact tubes pass. In a typical single reactor system, the first heat transfer zone generally corresponds to that portion of the reactor where the oxidation of propylene to acrolein predominantly occurs in the contact tubes. The first heat transfer zone not only maintains an appropriate temperature range, but also serves to heat the reactants to the reaction temperature. In a like manner, the second heat transfer zone corresponds to that portion of the reactor where oxidation of acrolein to acrylic acid predominantly occurs in the contact tubes, wherein the reactants are brought to second stage reaction temperature and then maintained at this temperature. It is also recognized that some oxidation to acrylic acid may occur in reaction zones A and A' and some oxidation of propylene to acrolein may occur in reaction zones B and B'. Furthermore, if used, either reaction may occur in zones A" and B". Accordingly, the contact tubes are arranged so that the appropriate reaction zones are positioned in the appropriate heat transfer zone.

Each heat transfer zone has circulating within it a heat transfer medium which is used to maintain an effective catalyst temperature profile and therefore reaction temperature. Maintaining a desired catalyst temperature profile is required for maintaining the optimum acrylic acid yield and for optimizing catalyst life. If the reaction temperature is too high, more carbon dioxide and carbon monoxide are formed thereby resulting in lower yields. Furthermore, the catalyst will age more quickly at excessive reaction temperatures. Of course, if the temperature gets high enough an uncontrolled runaway reaction may occur. If not controlled, such a reaction could lead to catalyst destruction and/or explosive conditions. If the reaction temperature is too low, less propylene will be converted to acrolein and acrolein to acrylic acid so that yields will be lower. If the reaction temperature is excessively low, a flammable mixture of propylene and/or acrolein may travel downstream leading to serious consequences.

The heat transfer medium circulates within each heat transfer zone thereby transferring heat from those outer portions of the contact tubes it contacts in the particular zone. The first heat transfer zone, corresponding to the oxidation of propylene to acrolein, is maintained at a temperature of 250 to 450, preferably 280 to 380° C. This first heat transfer zone may correspond to the heat transfer zone in the first stage reactor of a tandem system or the first stage heat transfer zone of a single reactor system. The second heat transfer zone, corresponding to the oxidation of acrolein to acrylic acid is maintained at a temperature of 220 to 450, preferably 240 to 360° C. This second heat transfer zone may correspond to the heat transfer zone in the second stage reactor of a tandem system or the second stage heat transfer zone of a single reactor system.

As explained above, it is to be understood that each reactor of a tandem system may be divided into two heat transfer zones to, for example, better control the temperature of the reaction. Likewise, each heat transfer zone of a single reactor system may be subdivided so as to provide individualized temperature control of sequential reaction zones in each stage, as described above.

Typically, the temperature difference of the heat transfer medium between point of entrance and point of exit from the oxidation reactor in a particular heat transfer zone is 2 to 12° C. The radial temperature gradient of the heat transfer medium in the oxidation reactor is 0.1 to 5° C. The peak catalyst temperatures are 20 to 70° C. above the heat transfer medium temperature and are very sensitive to changes in the heat transfer medium temperature. As is known in the art the catalyst will lose activity as it grows older. To compensate, reaction temperature must be increased to maintain production of acrolein and acrylic acid at desired levels.

The heat transfer medium may circulate in any manner deemed suitable for the particular reactor system utilized. In one embodiment, the heat transfer medium circulates within the reactor cocurrent with the flow of the reactant gasses through the reactor. It is understood that the cocurrent flow may proceed top to bottom, bottom to top or side to side in the reactor. In an alternative embodiment, the heat transfer medium circulates within the reactor countercurrent with the flow of the reactant gasses through the reactor. In another embodiment, the heat transfer medium circulates within the reactor both cocurrent with the flow of the reactant gasses and transverse both away from and towards the center of the reactor in a meandering flow. In another alternative embodiment, the heat transfer medium circulates within the reactor both countercurrent with the flow of the reactant gasses and transverse both away from and towards the center of the reactor in a meandering flow. In a further embodiment, a bypass flow of the heat transfer medium is provided. U.S.

Pat. Nos. 4,256,783; 5,151,605; 5,739,391; and DE 2,201,528, describe and disclose contact tube and baffle arrangements in contact tube fixed bed shell reactors which provide for cocurrent, countercurrent, transverse and bypass flows of the heat transfer medium, such references being incorporated herein by reference for their teaching of heat transfer medium flow and reactor arrangements to accomplish the same. Furthermore, it is understood that the baffles may be arranged so as to have equal spacing between baffles or variable spacing between baffles.

The heat transfer medium may be any heat transfer medium suitable for use under the temperature conditions of the present invention. Generally the heat transfer medium is a salt melt, preferably a salt melt of 40 to 80, preferably 50 to 70 percent by weight potassium nitrate and 60 to 20, preferably 50 to 30 percent by weight sodium nitrite. In an alternative embodiment, the salt melt may include sodium nitrate as a substitute for sodium nitrite or potassium nitrate or as an additional component of the salt melt. The sodium nitrate is generally present at up to 20, preferably up to 10 percent by weight of the total salt composition. Other examples of heat transfer mediums include heat transfer oils, both oleaginous and synthetic, heat transfer fluids such as phenyl ethers and polyphenyls, and low melting metals such as sodium, tin, mercury, as well as low melting alloys of various metals.

In one embodiment, the heat transfer medium circulates within the reactor in at least two distinct heat transfer medium circuits. In another embodiment, the heat transfer medium circulates within each reactor of a tandem reactor system in at least one distinct heat transfer medium circuit. Preferably, at least one circuit is in each heat transfer zone. In an alternative embodiment, the heat transfer circuit contains a cooling circuit whereby a portion of the heat transfer medium of each heat transfer medium circuit is circulated to the outside of the reactor for cooling and then returned to the heat transfer medium circuit. In a further embodiment, the heat transfer medium circulates within the reactor in at least two distinct heat transfer medium circuits at least one of which is a bypass circuit where at least a portion of the heat transfer medium circulates in a manner so as to bypass contact with at least a portion of the contact tubes. In an alternative embodiment, the at least two distinct heat transfer medium circuits include two distinct heat transfer medium circuits as well as both a cooling circuit and a bypass circuit.

Once produced, the hot mixed product gasses exit the reactor and are sent for further processing. As is known in the art, such further processing may include extraction, absorption and/or distillation processes to produce crude, glacial and/or flocculant grade acrylic acid.

The following Examples are provided as an illustration of the present invention; and utilize four different R1 catalysts, i.e. R1-A, R1-B, R1-C and R1-D and four different R2 catalysts, i.e. R2-A, R2-B, R2-C and R2-D. Abbreviations used throughout this application are:

° C.=degrees Centigrade mm=millimeters
% C3=volume percent of propylene
O2/C3=ratio of oxygen to propylene
% steam=volume percent steam or water vapor
R1-SV=Space velocity into first oxidation reactor ($hr^{-1}$)
R1 C3-SV=Propylene space velocity into first oxidation reactor ($hr^{-1}$)
R2-SV Space velocity into second oxidation reactor ($hr^{-1}$)
R2 C3-SV=Propylene space velocity into second oxidation reactor ($hr^{-1}$)

C3 Conv=percent propylene conversion
AA Yield=percent yield of acrylic acid
AA (lb/hr)/tube=pounds of acrylic acid produced per hour per contact tube

EXAMPLES 1–3

Examples 1–3 utilized a reactant mixture according to Table 1 having the indicated volume percent of reactive hydrocarbon, an amount of air and absorber off-gas sufficient to maintain the indicated oxygen/propylene ratio, and the indicated volume percent of water vapor which was fed to the contact tubes of a first shell and tube oxidation reactor of a tandem reactor system surrounded by a molten salt mixture for temperature control, each tube having an inner diameter of 39.3 mm. The reactants were introduced into the contact tubes, at the indicated reactive hydrocarbon space velocity (propylene space velocity), of a first oxidation reactor. The reactions were targeted to be maintained at a salt temperature between 310 to 330° C.

TABLE 1

| Ex. | % C3 | O2/C3 | % steam | R1-SV | R1 C3-SV | R2-SV | R2 C3-SV |
|---|---|---|---|---|---|---|---|
| 1 | 7.1 | 1.78 | 32.39 | 1142 | 81 | 1144 | 81 |
| 2 | 7.1 | 1.78 | 32.41 | 1342 | 95 | 1344 | 95 |
| 3 | 7.1 | 1.78 | 32.40 | 1547 | 109 | 1549 | 110 |

The contact tubes of the first oxidation reactor were packed with an R1 catalyst, designated R1-A, in two zones A and A'. Zone A was packed the R1-A catalyst diluted to 40% by volume with inert Denstone 57® catalyst bed supports available from Norton Chemical Products Corp., of Akron, Ohio so that zone A was 40% catalyst. Zone A' contained 100 percent of the R1-A catalyst. The ratio of the lengths of Zone A and Zone A', A/A', was 1.1.

The mixed product gas formed in the first oxidation reactor was then introduced into the contact tubes of a second shell and tube oxidation reactor of a tandem reactor system surrounded by a molten salt mixture for temperature control, each tube having an inner diameter of 39.3 mm. The contact tubes of the second oxidation reactor were packed with an R2 catalyst, designated R2-A, in two zones B and B'. Zone B was packed with the R2-A catalyst diluted to 40 percent by volume with inert Denstone 57® catalyst bed supports available from Norton Chemical Products Corp., of Akron, Ohio so that zone B was 40% catalyst. Zone B' contained 100 percent of the R2-A catalyst. The ratio of the lengths of Zone B and Zone B', B/B', was 0.7. The reactants were introduced into the contact tubes, at the indicated reactive hydrocarbon space velocity (R2 propylene space velocity), of a second oxidation reactor. The reactions were targeted to be maintained at a salt temperature between 250 to 270° C.

The acrylic acid yield (AA Yield) and process productivity (AA lbs/hr/tube) were calculated and are reported as relative values (i.e., Relative AA Yield of Example N (N=1–3)=(AA Yield of Example N)÷(AA Yield of Example 1) and Relative AA lbs/hr/tube of Example N (N=1–3)=(AA lbs/hr/tube of Example N)÷(AA lbs/hr/tube of Example 1)) in Table 2.

TABLE 2

| Ex. | Relative AA Yield | Relative AA lbs/hr /tube |
|---|---|---|
| 1 | 1.000 | 1.00 |
| 2 | 0.995 | 1.17 |
| 3 | 0.989 | 1.34 |

EXAMPLES 4–9

Examples 4–9 utilized a reactant mixture according to Table 3 having the indicated volume percent of reactive hydrocarbon, an amount of air and absorber off-gas sufficient to maintain the indicated oxygen/propylene ratio, and a volume percent of water vapor, which was fed to the contact tubes of a first shell and tube oxidation reactor of a tandem reactor system surrounded by a molten salt mixture for temperature control each tube having an inner diameter of 39.3 mm. The reactants were introduced into the contact tubes, at the indicated reactive hydrocarbon space velocity (propylene space velocity), of a first oxidation reactor. The reactions were targeted to be maintained at a salt temperature between 330 to 360° C.

TABLE 3

| Ex. | % C3 | O2/C3 | % steam | R1-SV | R1 C3-SV | R2-SV | R2 C3-SV |
|---|---|---|---|---|---|---|---|
| 4 | 7.0 | 1.79 | 32.39 | 1152 | 81 | 1158 | 82 |
| 5 | 7.1 | 1.77 | 32.39 | 1140 | 81 | 1145 | 82 |
| 6 | 7.1 | 1.79 | 32.39 | 1352 | 95 | 1358 | 96 |
| 7 | 7.1 | 1.78 | 32.39 | 1553 | 110 | 1560 | 110 |
| 8 | 7.1 | 1.78 | 32.39 | 1651 | 117 | 1658 | 117 |
| 9 | 7.1 | 1.78 | 32.40 | 1747 | 124 | 1755 | 125 |

The contact tubes of the first oxidation reactor were packed with an R1 catalyst, designated R1-B, in two zones A and A'. Zone A was packed with the R1-B catalyst diluted to 60% by volume with inert Denstone 57® catalyst bed supports available from Norton Chemical Products Corp., of Akron, Ohio so that zone A was 60% catalyst. Zone A' contained 100 percent of the R1-B catalyst. The ratio of the lengths of Zone A and Zone A', A/A', was 0.5.

The mixed product gas formed in the first oxidation reactor was then introduced into the contact tubes of a second shell and tube oxidation reactor of a tandem reactor system surrounded by a molten salt mixture for temperature control, each contact tube having an inner diameter of 39.3 mm. The contact tubes of the second oxidation reactor were packed with an R2 catalyst, designated R2-B, in two zones B and B'. Zone B was packed with the R2-B catalyst diluted to 78% by volume with inert Denstone 57® catalyst bed supports available from Norton Chemical Products Corp., of Akron, Ohio so that zone B was 78% catalyst. Zone B' contained 100 percent of the R2-B catalyst. The ratio of the lengths of Zone B and Zone B', B/B', was 0.5. The reactants were introduced into the contact tubes, at the indicated reactive hydrocarbon space velocity (R2 propylene space velocity), of a second oxidation reactor. The reactions were targeted to be maintained at a salt temperature between 270 to 300° C.

The acrylic acid yield (AA Yield) and process productivity (AA lbs/hr/tube) were calculated and are reported as relative values (i.e., Relative AA Yield Of Example N (N=4–9)=(AA Yield of Example N)÷(AA Yield of Example 4) and Relative AA lbs/hr/tube of Example N (N=4–9)=(AA lbs/hr/tube of Example N)÷(AA lbs/hr/tube of Example 4)) in Table 4.

TABLE 4

| Ex. | Relative AA Yield | Relative AA lbs/hr /tube |
|---|---|---|
| 4 | 1.000 | 1.00 |
| 5 | 1.005 | 1.00 |
| 6 | 0.994 | 1.16 |
| 7 | 0.985 | 1.33 |
| 8 | 0.979 | 1.41 |
| 9 | 0.969 | 1.48 |

EXAMPLES 10–26

Examples 10–26 utilized a reactant mixture according to Table 5 having the indicated volume percent of reactive hydrocarbon, an amount of air and absorber off-gas sufficient to maintain the indicated oxygen/propylene ratio, and the indicated volume percent of water vapor which was fed to the contact tubes of a shell and tube oxidation reactor of a single reactor system surrounded by a molten salt mixture for temperature control, each contact tube having an inner diameter of 25.2 mm. The reactants were introduced into the contact tubes, at the indicated reactive hydrocarbon space velocity (propylene space velocity), of the oxidation reactor. The reactions were targeted to be maintained at a salt temperature between 325 to 350° C. in the first stage (R1) and 275 to 300° C. in the second stage (R2).

TABLE 5

| Ex. | % C3 | O2/C3 | % steam | R1-SV | R1 C3-SV | R2-SV | R2 C3-SV |
|---|---|---|---|---|---|---|---|
| 10 | 7.0 | 1.79 | 9.97 | 1677 | 117 | 1646 | 115 |
| 11 | 7.0 | 1.78 | 9.97 | 1670 | 118 | 1639 | 115 |
| 12 | 7.1 | 1.78 | 9.96 | 1668 | 118 | 1638 | 116 |
| 13 | 7.1 | 1.77 | 9.96 | 1669 | 118 | 1639 | 116 |
| 14 | 7.0 | 1.79 | 9.99 | 2011 | 141 | 1974 | 139 |
| 15 | 7.1 | 1.78 | 9.95 | 2006 | 141 | 1969 | 139 |
| 16 | 7.0 | 1.79 | 9.95 | 2282 | 161 | 2241 | 158 |
| 17 | 8.0 | 1.79 | 9.95 | 2005 | 161 | 1968 | 158 |
| 18 | 8.1 | 1.78 | 9.95 | 1997 | 161 | 1961 | 158 |
| 19 | 7.1 | 1.78 | 9.95 | 2293 | 162 | 2251 | 159 |
| 20 | 7.0 | 1.79 | 9.98 | 2512 | 177 | 2466 | 174 |
| 21 | 8.0 | 1.78 | 9.97 | 2202 | 177 | 2162 | 174 |
| 22 | 8.0 | 1.78 | 9.99 | 2492 | 201 | 2447 | 197 |
| 23 | 8.1 | 1.78 | 9.98 | 2491 | 201 | 2446 | 197 |
| 24 | 8.0 | 1.79 | 6.98 | 2782 | 224 | 2731 | 220 |
| 25 | 8.1 | 1.78 | 6.99 | 2779 | 224 | 2728 | 220 |
| 26 | 8.1 | 1.78 | 6.99 | 2771 | 224 | 2721 | 220 |

The contact tubes of the oxidation reactor were packed with R1-A and R2-A catalysts, as utilized in Examples 1–3, in four zones A, A', B, and B'. Zone A was packed with the R1-A catalyst diluted to 66% by volume with inert Denstone 57® catalyst bed supports available from Norton Chemical Products Corp., of Akron, Ohio so that zone A was 66% catalyst. Zone A' contained 100 percent of the R1-A catalyst. The ratio of the lengths of Zone A and Zone A', A/A', was 0.4. Zone B was packed with the R2-A catalyst diluted to 70% by volume with inert Denstone 57® catalyst bed supports available from Norton Chemical Products Corp., of Akron, Ohio so that zone A was 70% catalyst. Zone B' contained 100 percent of the R2-A catalyst. The ratio of the lengths of Zone B and Zone B', B/B', was 0.4.

The acrylic acid yield (AA Yield) and process productivity (AA lbs/hr/tube) were calculated and are reported as relative values (i.e., Relative AA Yield of Example N (N=10–26)=(AA Yield of Example N (N=10–26)÷(AA Yield of Example 10) and Relative AA lbs/hr/tube of Example N (N=10–26)=(AA lbs/hr/tube of Example N)÷(AA lbs/hr/tube of Example 10)) in Table 6.

TABLE 6

| Ex. | Relative AA Yield | Relative AA lbs/hr /tube |
|---|---|---|
| 10 | 1.000 | 1.00 |
| 11 | 1.001 | 1.01 |
| 12 | 1.001 | 1.01 |
| 13 | 0.997 | 1.01 |
| 14 | 0.989 | 1.19 |
| 15 | 0.989 | 1.19 |
| 16 | 0.983 | 1.35 |
| 17 | 0.979 | 1.35 |
| 18 | 0.978 | 1.35 |
| 19 | 0.982 | 1.36 |
| 20 | 0.976 | 1.47 |
| 21 | 0.974 | 1.47 |
| 22 | 0.964 | 1.65 |
| 23 | 0.964 | 1.65 |
| 24 | 0.949 | 1.81 |
| 25 | 0.950 | 1.82 |
| 26 | 0.943 | 1.81 |

EXAMPLES 27–33

Examples 27–33 utilized a reactant mixture according to Table 7 having the indicated volume percent of reactive hydrocarbon, an amount of air and absorber off-gas sufficient to maintain the indicated oxygen/propylene ratio, and the indicated volume percent of water vapor which was fed to the contact tubes of a shell and tube oxidation reactor of a single reactor system surrounded by a molten salt mixture for temperature control, each contact tube having an inner diameter of 25.2 mm. The reactants were introduced into the contact tubes, at the indicated reactive hydrocarbon space velocity (propylene space velocity), of the oxidation reactor. The reactions were targeted to be maintained at a salt temperature between 340 to 360° C. in the first stage (R1) and 280 to 300° C. in the second stage (R2).

TABLE 7

| Ex. | % C3 | O2/C3 | % steam | R1-SV | R1 C3-SV | R2-SV | R2 C3-SV |
|---|---|---|---|---|---|---|---|
| 27 | 7.0 | 1.78 | 9.96 | 1659 | 117 | 1645 | 116 |
| 28 | 7.1 | 1.78 | 9.97 | 1650 | 117 | 1636 | 116 |
| 29 | 7.0 | 1.78 | 10.00 | 1659 | 117 | 1645 | 116 |
| 30 | 7.1 | 1.78 | 9.96 | 1655 | 117 | 1641 | 116 |
| 31 | 7.1 | 1.78 | 9.97 | 1982 | 140 | 1965 | 139 |
| 32 | 7.1 | 1.78 | 9.97 | 2321 | 164 | 2301 | 162 |
| 33 | 7.1 | 1.78 | 9.97 | 2484 | 175 | 2463 | 174 |

The contact tubes of the oxidation reactor were packed with R1 and R2 catalysts, designated as R1-C and R2-C, respectively, in two zones A and B. Zone A was packed with 100% of the R1-C catalyst. Zone B was packed with 100% of the R2-C catalyst. The ratio of the lengths of Zone A and Zone B, A/B, was 1.0.

The acrylic acid yield (AA Yield) and process productivity (AA lbs/hr/tube) were calculated and are reported as relative values (i.e., Relative AA Yield of Example N (N=27–33)=(AA Yield of Example N)÷(AA Yield of Example 27) and Relative AA lbs/hr/tube of Example N (N=27–33)=(AA lbs/hr/tube of Example N)÷(AA lbs/hr/tube of Example 27) in Table 8.

TABLE 8

| Ex. | Relative AA Yield | Relative AA lbs/hr /tube |
|---|---|---|
| 27 | 1.000 | 1.00 |
| 28 | 0.997 | 0.99 |
| 29 | 1.000 | 1.00 |
| 30 | 1.000 | 1.00 |
| 31 | 0.992 | 1.18 |
| 32 | 0.986 | 1.38 |
| 33 | 0.981 | 1.47 |

EXAMPLES 34–44

Examples 34–44 utilized a reactant mixture according to Table 9 having the indicated volume percent of reactive hydrocarbon, an amount of air and absorber off-gas sufficient to maintain the indicated oxygen/propylene ratio, and the indicated volume percent of water vapor which was fed to the contact tubes of a shell and tube oxidation reactor of a single reactor system surrounded by a molten salt mixture for temperature control, each contact tube having an inner diameter of 25.2 mm. The reactants were introduced into the contact tubes, at the indicated reactive hydrocarbon space velocity (propylene space velocity), of the oxidation reactor. The reactions were targeted to be maintained at a salt temperature between 320 to 340° C. in the first stage (R1) and 280 to 300° C. in the second stage (R2).

TABLE 9

| Ex. | % C3 | O2/C3 | % steam | R1-SV | R1 C3-SV | R2-SV | R2 C3-SV |
|---|---|---|---|---|---|---|---|
| 34 | 6.99 | 1.87 | 9.62 | 1656 | 116 | 1905 | 133 |
| 35 | 7.22 | 1.89 | 7.35 | 1604 | 116 | 1845 | 133 |
| 36 | 6.97 | 1.84 | 9.65 | 1737 | 121 | 1998 | 139 |
| 37 | 7.04 | 1.89 | 8.10 | 1794 | 126 | 2064 | 145 |
| 38 | 7.13 | 1.88 | 8.06 | 1771 | 126 | 2038 | 145 |
| 39 | 7.24 | 1.87 | 7.87 | 1744 | 126 | 2007 | 145 |
| 40 | 6.96 | 1.87 | 9.50 | 1890 | 132 | 2174 | 151 |
| 41 | 7.30 | 1.86 | 7.86 | 1802 | 132 | 2073 | 151 |
| 42 | 7.22 | 1.86 | 8.91 | 1895 | 137 | 2180 | 157 |
| 43 | 7.43 | 1.82 | 8.33 | 1841 | 137 | 2118 | 157 |
| 44 | 7.28 | 1.86 | 8.70 | 1951 | 142 | 2244 | 163 |

The contact tubes of the oxidation reactor were packed with R1 and R2 catalysts, designated as R1-D and R2-D, respectively, in two zones A, and B. Zone A was packed with 100% of the R1-D catalyst. Zone B was packed with 100% of the R2-D catalyst. The ratio of the lengths of Zone A and Zone B, was 1.2.

The acrylic acid yield (AA Yield) and process productivity (AA lbs/hr/tube) were calculated and are reported as relative values (i.e., Relative AA Yield of Example N (N=34–44)=(AA Yield of Example N)÷(AA Yield of Example 34) and Relative AA lbs/hr/tube of Example N (N=34–44)=(AA lbs/hr/tube of Example N)÷(AA lbs/hr/tube of Example 34) in Table 10.

TABLE 10

| Ex. | Relative AA Yield | Relative AA lbs/hr /tube |
|---|---|---|
| 34 | 1.000 | 1.00 |
| 35 | 1.000 | 1.00 |
| 36 | 0.999 | 1.05 |
| 37 | 1.005 | 1.10 |
| 38 | 1.001 | 1.10 |
| 39 | 1.002 | 1.10 |
| 40 | 0.996 | 1.14 |
| 41 | 0.998 | 1.14 |
| 42 | 0.993 | 1.18 |
| 43 | 0.994 | 1.18 |
| 44 | 0.991 | 1.22 |

EXAMPLES 45–61

Examples 45–61 utilized a reactant mixture according to Table 11 having the indicated volume percent of reactive hydrocarbon, an amount of air and absorber off-gas sufficient to maintain the indicated oxygen/propylene ratio, and the indicated volume percent of water vapor were fed to the contact tubes of a shell and tube oxidation reactor of a single reactor system surrounded by a molten salt mixture for temperature control, each contact tube having an inner diameter of 25.2 mm. The reactants were introduced into the contact tubes, at the indicated reactive hydrocarbon space velocity (propylene space velocity), of the oxidation reactor. The reactions were targeted to be maintained at a salt temperature between 310 to 330° C. in the first stage (R1) and 275 to 305° C. in the second stage (R2).

TABLE 11

| Ex. | % C3 | O2/C3 | % steam | R1-SV | R1 C3-SV | R2-SV | R2 C3-SV |
|---|---|---|---|---|---|---|---|
| 45 | 7.14 | 1.82 | 9.06 | 1435 | 102 | 1650 | 118 |
| 46 | 7.48 | 1.88 | 7.59 | 1371 | 103 | 1577 | 118 |
| 47 | 7.55 | 1.87 | 7.30 | 1354 | 102 | 1558 | 118 |
| 48 | 7.54 | 1.88 | 7.37 | 1494 | 113 | 1719 | 130 |
| 49 | 7.49 | 1.87 | 7.45 | 1638 | 123 | 1885 | 141 |
| 50 | 7.50 | 1.87 | 7.49 | 1707 | 128 | 1964 | 147 |
| 51 | 7.75 | 1.84 | 7.25 | 1718 | 133 | 1977 | 153 |
| 52 | 7.51 | 1.87 | 7.53 | 1841 | 138 | 2118 | 159 |
| 53 | 8.00 | 1.83 | 7.03 | 1761 | 141 | 2025 | 162 |
| 54 | 7.99 | 1.84 | 6.76 | 1822 | 146 | 2096 | 168 |
| 55 | 7.96 | 1.83 | 6.78 | 1868 | 149 | 2149 | 171 |
| 56 | 8.01 | 1.82 | 6.78 | 1886 | 151 | 2169 | 174 |
| 57 | 7.71 | 1.84 | 7.18 | 1992 | 154 | 2291 | 177 |
| 58 | 7.86 | 1.83 | 7.44 | 1954 | 154 | 2248 | 177 |
| 59 | 8.01 | 1.87 | 6.91 | 1920 | 154 | 2209 | 177 |
| 60 | 8.01 | 1.85 | 6.57 | 1925 | 154 | 2215 | 177 |
| 61 | 8.01 | 1.85 | 6.93 | 1950 | 156 | 2243 | 180 |

The contact tubes of the oxidation reactor were packed with R1-D and R2-D catalysts, as utilized in Examples 33–44, in two zones A and B. Zone A was packed with 100% of the R1-D catalyst. Zone B was packed with 100% of the R2-D catalyst. The ratio of the lengths of Zone A and Zone B, A/B, was 1.2.

The acrylic acid yield (AA Yield) and process productivity (AA lbs/hr/tube) were calculated and are reported as relative values (i.e., Relative AA Yield of Example N (N=45–61)=(AA Yield of Example N)÷(AA Yield of Example 45) and Relative AA lbs/hr/tube of Example N (N=45–61)=(AA lbs/hr/tube of Example N)÷(AA lbs/hr/tube of Example 45)) in Table 12.

TABLE 12

| Ex. | Relative AA Yield | Relative AA lbs/hr /tube |
|---|---|---|
| 45 | 1.000 | 1.00 |
| 46 | 0.993 | 1.00 |
| 47 | 0/986 | 0.99 |
| 48 | 0.981 | 1.08 |
| 49 | 0.987 | 1.18 |
| 50 | 0.989 | 1.24 |
| 51 | 0.985 | 1.28 |
| 52 | 0.982 | 1.33 |
| 53 | 0.985 | 1.36 |
| 54 | 0.979 | 1.39 |
| 55 | 0.978 | 1.42 |
| 56 | 0.977 | 1.45 |
| 57 | 0.973 | 1.47 |
| 58 | 0.976 | 1.47 |
| 59 | 0.980 | 1.48 |
| 60 | 0.974 | 1.47 |
| 61 | 0.976 | 1.50 |

We claim:

1. A catalytic vapor phase oxidation process, comprising:
(A) providing an oxidation reactor comprising a plurality of contact tubes disposed in a reactor shell, the inside of the reactor shell being divided into at least first and second heat transfer zones through each of which a heat transfer medium passes; each of said contact tubes containing at least two sequentially disposed oxidation catalysts, said at least two oxidation catalysts being jointly capable of effecting the oxidation of a reactive hydrocarbon to a product gas comprising (meth)acrylic acid, a first oxidation catalyst in said sequence being capable of effecting the oxidation of a reactive hydrocarbon to (meth)acrolein and being substantially located in that portion of each contact tube in contact with the first heat transfer zone, a second oxidation catalyst in said sequence being capable of effecting the oxidation of (meth)acrolein to (meth)acrylic acid and being substantially located in that portion of each contact tube in contact with the second heat transfer zone; said contact tubes containing said at least two oxidation catalysts being packed with said at least two oxidation catalysts in such a manner so as to provide a peak-to-salt temperature sensitivity of not more than 9° C.; and
(B) feeding a reactant composition comprising
(i) at least one reactive hydrocarbon, and
(ii) oxygen
into said oxidation reactor, at a reactive hydrocarbon space velocity of from 135 $hr^{-1}$ to 300 $hr^{-1}$, to contact said reactant composition with said at least two oxidation catalysts to form a product gas comprising (meth)acrylic acid;
wherein, when said portion of each contact tube in contact with the first heat transfer zone comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is less than +5° C.;
wherein, when said portion of each contact tube in contact with the second heat transfer zone comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

2. A catalytic vapor phase oxidation process, comprising:
(A) providing a first oxidation reactor comprising a plurality of contact tubes disposed in a reactor shell, the inside of the reactor shell being divided into at least a first heat transfer zone through each of which a heat transfer medium passes; each of said contact tubes containing at least one first oxidation catalyst, said at least one first oxidation catalyst being capable of effecting the oxidation of a first reactive hydrocarbon and oxygen to a first product gas comprising at least one second reactive hydrocarbon and oxygen, said contact tubes containing at least one first oxidation catalyst being packed in such a manner so as to provide a peak-to-salt temperature sensitivity of not more than 9° C.;
(B) feeding said first reactant composition comprising
(i) at least one first reactive hydrocarbon, and
(ii) oxygen
into said first oxidation reactor, at a first reactive hydrocarbon space velocity of from 135 hr$^{-1}$ to 300 hr$^{-1}$, to contact said first reactant composition with at least one first oxidation catalyst to form a first product gas comprising at least one second reactive hydrocarbon and oxygen;
wherein, when each said contact tube of said first oxidation reactor comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is less than +5° C.;
(C) providing a second oxidation reactor comprising a plurality of contact tubes disposed in a reactor shell, the inside of the reactor shell being divided into at least a first heat transfer zone through each of which a heat transfer medium passes; each of said contact tubes containing at least one second oxidation catalyst, said at least one second oxidation catalyst being capable of effecting the oxidation of said second reactive hydrocarbon and oxygen to a final product gas comprising (meth)acrylic acid, said contact tubes containing at least one second oxidation catalyst being packed with said at least one second catalyst in such a manner so as to provide a peak-to-salt temperature sensitivity of not more than 9° C.;
(D) feeding said first product gas comprising
(i) at least one second reactive hydrocarbon, and
(ii) oxygen
into said second oxidation reactor, at a second reactive hydrocarbon space velocity of from 135 hr$^{-1}$ to 300 hr$^{-1}$; to contact said first product gas with said at least one second oxidation catalyst to form a final product gas comprising (meth)acrylic acid;
wherein, when each said contact tube of said second oxidation reactor comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

3. A catalytic vapor phase oxidation process, comprising:
(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of—a reactant composition comprising at least one reactive hydrocarbon selected from the group consisting of acrolein, methacrolein, and mixtures thereof and oxygen into a product gas comprising (meth)acrylic acid, said contact tubes containing at least one oxidation catalyst being packed with said at least one oxidation catalyst in such a manner so as to provide a peak-to-salt temperature sensitivity of not more than 9° C.;
(B) feeding a reactant composition comprising
(i) at least one reactive hydrocarbon selected from the group consisting of acrolein, methacrolein, and mixtures thereof, and
(ii) oxygen
into said oxidation reactor, at a reactive hydrocarbon space velocity of from 135 hr$^{-1}$ to 300 hr$^{-1}$, to contact said reactant composition with said at least one oxidation catalyst to form a product gas comprising (meth)acrylic acid;
wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is less than +5° C.

4. A catalytic vapor phase oxidation process, comprising:
(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising: at least one reactive hydrocarbon selected from the group consisting of propylene, isobutylene, and mixtures thereof and oxygen into a product gas comprising (meth)acrolein, said contact tubes containing at least one oxidation catalyst being packed with said at least one oxidation catalyst in such a manner so as to provide a peak-to-salt temperature sensitivity of not more than 9° C.;
(B) feeding a reactant composition comprising
(i) at least one reactive hydrocarbon selected from the group consisting of propylene, isobutylene, and mixtures thereof, and
(ii) oxygen
into said oxidation reactor, at a reactive hydrocarbon space velocity of from 135 hr$^{-1}$ to 300 hr$^{-1}$ to contact said reactant composition with said at least one oxidation catalyst to form a product gas comprising (meth)acrolein;
wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is less than +5° C.

5. A catalytic vapor phase oxidation process, comprising:
(A) providing an oxidation reactor comprising a plurality of contact tubes disposed in a reactor shell, the inside of the reactor shell being divided into at least first and second heat transfer zones through each of which a heat transfer medium passes; each of said contact tubes containing at least two sequentially disposed oxidation catalysts, said at least two oxidation catalysts being jointly capable of effecting the oxidation of a reactive hydrocarbon to a product gas comprising (meth)acrylic acid, a first oxidation catalyst in said sequence being capable of effecting the oxidation of a reactive hydrocarbon to (meth)acrolein and being substantially located in that portion of each contact tube in contact with the first heat transfer zone, a second oxidation catalyst in said sequence being capable of effecting the oxidation of (meth)acrolein to (meth)acrylic acid and being substantially located in that portion of each contact tube in contact with the second heat transfer zone; said contact tubes containing said at least two oxidation catalysts being packed with said at least two oxidation catalysts in such a manner so as to provide a peak-to-salt temperature sensitivity of not more than 9° C.; and (B) feeding a reactant composition comprising
   (i) at least one reactive hydrocarbon,
   (ii) oxygen,
   (iii) less than 15,% by volume of the reactant composition of carbon oxides, and
   (iv) less than 15% by volume of the reactant composition of inert gas fuel,
      with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$, to contact said reactant composition with said at least two oxidation catalysts to form a product gas comprising (meth)acrylic acid;
   wherein, when said portion of each contact tube in contact with the first heat transfer zone comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is less than +5° C.;
   wherein, when said portion of each contact tube in contact with the second heat transfer zone comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

6. A catalytic vapor phase oxidation process, comprising:

(A) providing a first oxidation reactor comprising a plurality of contact tubes disposed in a reactor shell, the inside of the reactor shell being divided into at least a first heat transfer zone through each of which a heat transfer medium passes; each of said contact tubes containing at least one first oxidation catalyst, said at least one first oxidation catalyst being capable of effecting the oxidation of a first reactive hydrocarbon and oxygen to a first product gas comprising at least one second reactive hydrocarbon and oxygen, said contact tubes containing at least one first oxidation catalyst being packed in such a manner so as to provide a peak-to-salt temperature sensitivity of not more than 9° C.;

(B) feeding said first reactant composition comprising
   (i) at least one first reactive hydrocarbon, and
   (ii) oxygen,
   (iii) less than 15% by volume of the reactant composition of carbon oxides, and
   (iv) less than 15% by volume of the reactant composition of inert gas fuel,
      with the proviso that the combined amount of carbon oxides and inert gas fuel present in the reactant composition is less than 15% by volume of the reactant composition,
into said first oxidation reactor, at a first reactive hydrocarbon space velocity of from 135 hr$^{-1}$ to 300 hr$^{-1}$, to contact said first reactant composition with at least one first oxidation catalyst to form a first product gas comprising at least one second reactive hydrocarbon and oxygen;
   wherein, when each said contact tube of said first oxidation reactor comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is less than +5° C.;

(C) providing a second oxidation reactor comprising a plurality of contact tubes disposed in a reactor shell, the inside of the reactor shell being divided into at least a first heat transfer zone through each of which a heat transfer medium passes; each of said contact tubes containing at least one second oxidation catalyst, said at least one second oxidation catalyst being capable of effecting the oxidation of said second reactive hydrocarbon and oxygen to a final product gas comprising (meth)acrylic acid, said contact tubes containing at least one second oxidation catalyst being packed with said at least one second catalyst in such a manner so as to provide a peak-to-salt temperature sensitivity of not more than 9° C.;

(D) feeding said first product gas comprising
   (i) at least one second reactive hydrocarbon, and
   (ii) oxygen
into said second oxidation reactor, at a second reactive hydrocarbon space velocity of from 135 hr$^{-1}$ to 300 hr$^{-1}$; to contact said first product gas with said at least one second oxidation catalyst to form a final product gas comprising (meth)acrylic acid;
   wherein, when each said contact tube of said second oxidation reactor comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

7. A catalytic vapor phase oxidation process, comprising:

(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of—a reactant composition comprising at least one reactive hydrocarbon selected from the group consisting of acrolein, methacrolein, and mixtures thereof and oxygen into a product gas comprising (meth)acrylic acid, said contact tubes containing at least one oxidation catalyst being packed with said at least one oxidation catalyst in such a manner so as to provide a peak-to-salt temperature sensitivity of not more than 9° C.;

(B) feeding a reactant composition comprising
   (i) at least one reactive hydrocarbon selected from the group consisting of acrolein, methacrolein, and mixtures thereof,
   (ii) oxygen,
   (iii) less than 15% by volume of the reactant composition of carbon oxides, and (iv) less than 15% by volume of the reactant composition of inert gas fuel,
with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$, to contact said reactant composition with said at least one oxidation catalyst to form a product gas comprising (meth)acrylic acid;
wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is less than +5° C.

8. A catalytic vapor phase oxidation process, comprising:
(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising: at least one reactive hydrocarbon selected from the group consisting of propylene, isobutylene, and mixtures thereof and oxygen into a product gas comprising (meth)acrolein, said contact tubes containing at least one oxidation catalyst being packed with said at least one oxidation catalyst in such a manner so as to provide a peak-to-salt temperature sensitivity of not more than 9° C.;
(B) feeding a reactant composition comprising
(i) at least one reactive hydrocarbon selected from the group consisting of propylene, isobutylene, and mixtures thereof, and
(ii) oxygen,
(iii) less than 15% by volume of the reactant composition of carbon oxides, and
(iv) less than 15% by volume of the reactant composition of inert gas fuel,
with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$ to contact said reactant composition with said at least one oxidation catalyst to form a product gas comprising (meth)acrolein;
wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is less than +5° C.

9. A catalytic vapor phase oxidation process, comprising:
(A) providing an oxidation reactor comprising a plurality of contact tubes disposed in a reactor shell, the inside of the reactor shell being divided into at least first and second heat transfer zones through each of which a heat transfer medium passes; each of said contact tubes containing at least two sequentially disposed oxidation catalysts, said at least two oxidation catalysts being jointly capable of effecting the oxidation of a reactive hydrocarbon to a product gas comprising (meth)acrylic acid, a first oxidation catalyst in said sequence being capable of effecting the oxidation of a reactive hydrocarbon to (meth)acrolein and being substantially located in that portion of each contact tube in contact with the first heat transfer zone, a second oxidation catalyst in said sequence being capable of effecting the oxidation of (meth)acrolein to (meth)acrylic acid and being substantially located in that portion of each contact tube in contact with the second heat transfer zone; said contact tubes containing said at least two oxidation catalysts being packed with said at least two oxidation catalysts in such a manner so as to provide a peak-to-salt temperature sensitivity of not more than 9° C.; and
(B) feeding a reactant composition comprising
(i) at least one reactive hydrocarbon,
(ii) oxygen,
(iii) less than 15% by volume of the reactant composition of carbon oxides, and
(iv) less than 15% by volume of the reactant composition of inert gas fuel,
with the proviso that the combined amount of carbon oxides and inert gas fuel present in the reactant composition is less than 15% by volume of the reactant composition,
into said oxidation reactor, at a reactive hydrocarbon space velocity of from 135 hr$^{-1}$ to 300 hr$^{-1}$, to contact said reactant composition with said at least two oxidation catalysts to form a product gas comprising (meth)acrylic acid;
wherein, when said portion of each contact tube in contact with the first heat transfer zone comprises a plurality of sequentially disposed reaction zones, the temperature differential, $T_{SR1}-T_{IP}$, between the temperature of each subsequent reaction zone, $T_{SR1}$, and the temperature of its immediately preceding reaction zone, $T_{IP1}$, is greater than +5° C.;
wherein, when said portion of each contact tube in contact with the second heat transfer zone comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is less than +5° C.

10. A catalytic vapor phase oxidation process, comprising:
(A) providing a first oxidation reactor comprising a plurality of contact tubes disposed in a reactor shell, the inside of the reactor shell being divided into at least a first heat transfer zone through each of which a heat transfer medium passes; each of said contact tubes containing at least one first oxidation catalyst, said at least one first oxidation catalyst being capable of effecting the oxidation of a first reactive hydrocarbon and oxygen to a first product gas comprising at least one second reactive hydrocarbon and oxygen, said contact tubes containing at least one first oxidation catalyst being packed in such a manner so as to provide a peak-to-salt temperature sensitivity of not more than 9° C.;
(B) feeding said first reactant composition comprising
(i) at least one first reactive hydrocarbon, and
(ii) oxygen,
(iii) less than 15% by volume of the reactant composition of carbon oxides, and
(iv) less than 15% by volume of the reactant composition of inert gas fuel,
with the proviso that the combined amount of carbon oxides and inert gas fuel present in the reactant composition is less than 15% by volume of the reactant composition, into said first oxidation reactor, at a first reactive hydrocarbon space velocity of from 135 hr$^{-1}$ to 300 hr$^{-1}$, to contact said first reactant composition with at least one first oxidation catalyst to form a first product gas comprising at least one second reactive hydrocarbon, oxygen, carbon oxides and inert gas fuel;

wherein, when each said contact tube of said first oxidation reactor comprises a plurality of sequentially disposed reaction zones, the temperature differential, $T_{SR1}-T_{IP1}$, between the temperature of each subsequent reaction zone, $T_{SR1}$, and the temperature of its immediately preceding reaction zone, $T_{IP1}$, is greater than +5° C.;

(C) providing a second oxidation reactor comprising a plurality of contact tubes disposed in a reactor shell, the inside of the reactor shell being divided into at least a first heat transfer zone through each of which a heat transfer medium passes; each of said contact tubes containing at least one second oxidation catalyst, said at least one second oxidation catalyst being capable of effecting the oxidation of said second reactive hydrocarbon and oxygen to a final product gas comprising (meth)acrylic acid, said contact tubes containing at least one second oxidation catalyst being packed with said at least one second catalyst in such a manner so as to provide a peak-to-salt temperature sensitivity of not more than 9° C.;

(D) feeding said first product gas comprising
  (i) at least one second reactive hydrocarbon,
  (ii) oxygen,
  (iii) carbon oxides, and
  (iv) inert gas fuel into said second oxidation reactor, at a second reactive hydrocarbon space velocity of from 135 hr$^{-1}$ to 300 hr$^{-1}$; to contact said first product gas with said at least one second oxidation catalyst to form a final product gas comprising (meth)acrylic acid;

wherein, when each said contact tube of said second oxidation reactor comprises a plurality of sequentially disposed reaction zones, the temperature differential, $T_{SR2}-T_{IP2}$, between the temperature of each subsequent reaction zone, $T_{SR2}$, and the temperature of its immediately preceding reaction zone, $T_{IP2}$, is greater than +5° C.

11. A catalytic vapor phase oxidation process, comprising:
(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of—a reactant composition comprising at least one reactive hydrocarbon selected from the group consisting of acrolein, methacrolein, and mixtures thereof and oxygen into a product gas comprising (meth)acrylic acid, said contact tubes containing at least one oxidation catalyst being packed with said at least one oxidation catalyst in such a manner so as to provide a peak-to-salt temperature sensitivity of not more than 9° C.;

(B) feeding a reactant composition comprising
  (i) at least one reactive hydrocarbon selected from the group consisting of acrolein, methacrolein, and mixtures thereof,
  (ii) oxygen,
  (iii) less than 15% by volume of the reactant composition of carbon oxides, and
  (iv) less than 15% by volume of the reactant composition of inert gas fuel,
    with the proviso that the combined amount of carbon oxides and inert gas fuel present in the reactant composition is less than 15% by volume of the reactant composition, into said oxidation reactor, at a reactive hydrocarbon space velocity of from 135 hr$^{-1}$ to 300 hr$^{-1}$, to contact said reactant composition with said at least one oxidation catalyst to form a product gas comprising (meth)acrylic acid;

wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is greater than +5° C.

12. A catalytic vapor phase oxidation process, comprising:
(A) providing an oxidation reactor comprising a plurality of contact tubes disposed in a reactor shell, the inside of the reactor shell being divided into at least one heat transfer zone through which a heat transfer medium passes; each of said contact tubes containing at least one oxidation catalyst, said at least one oxidation catalyst being capable of effecting the oxidation of a reactant composition comprising: at least one reactive hydrocarbon selected from the group consisting of propylene, isobutylene, and mixtures thereof and oxygen into a product gas comprising (meth)acrolein, said contact tubes containing at least one oxidation catalyst being packed with said at least one oxidation catalyst in such a manner so as to provide a peak-to-salt temperature sensitivity of not more than 9° C.;

(B) feeding a reactant composition comprising
  (i) at least one reactive hydrocarbon selected from the group consisting of propylene, isobutylene, and mixtures thereof,
  (ii) oxygen,
  (iii) less than 15% by volume of the reactant composition of carbon oxides, and
  (iv) less than 15% by volume of the reactant composition of inert gas fuel,
    with the proviso that the combined amount of carbon oxides and inert gas fuel present in the reactant composition is less than 15% by volume of the reactant composition, into said oxidation reactor, at a reactive hydrocarbon space velocity of from 135 hr$^{-1}$ to 300 hr$^{-1}$ to contact said reactant composition with said at least one oxidation catalyst to form a product gas comprising (meth)acrolein;

wherein, when each said contact tube comprises a plurality of sequentially disposed reaction zones, the temperature differential, $T_{SR}-T_{IP}$, between the temperature of each subsequent reaction zone, $T_{SR}$, and the temperature of its immediately preceding reaction zone, $T_{IP}$, is greater than +5° C.

\* \* \* \* \*